(12) United States Patent
Thomas, Jr. et al.

(10) Patent No.: US 6,680,168 B2
(45) Date of Patent: Jan. 20, 2004

(54) PASSIVE IMMUNIZATION AGAINST CLOSTRIDIUM DIFFICILE DISEASE

(75) Inventors: William D. Thomas, Jr., Somerville, MA (US); Paul J. Giannasca, Newton, MA (US); Zhenxi Zhang, Cambridge, MA (US); Wende Lei, Cambridge, MA (US); Thomas P. Monath, Harvard, MA (US)

(73) Assignee: Acambis, Inc., Cambridge, MA (US)

( * ) Notice: Subject to any disclaimer, the term of this patent is extended or adjusted under 35 U.S.C. 154(b) by 0 days.

(21) Appl. No.: 09/815,452

(22) Filed: Mar. 22, 2001

(65) Prior Publication Data

US 2001/0051153 A1 Dec. 13, 2001

Related U.S. Application Data

(63) Continuation of application No. 09/176,076, filed on Oct. 20, 1998, now Pat. No. 6,214,341.
(60) Provisional application No. 60/062,522, filed on Oct. 20, 1997.

(51) Int. Cl.[7] .............................. C12Q 1/00; C12N 5/06; A61K 39/395; C07K 16/00
(52) U.S. Cl. ........................... 435/4; 435/326; 435/340; 424/130.1; 424/150.1; 424/164.1; 424/167.1; 424/234.1; 424/236.1; 530/389.1; 530/389.5
(58) Field of Search ........................... 424/130.1, 150.1, 424/164.1, 167.1, 142.1, 234.1, 236.1, 239.1, 267.1; 530/389.1, 389.5; 435/4, 326, 340

(56) References Cited

U.S. PATENT DOCUMENTS

| | | |
|---|---|---|
| 5,412,077 A | 5/1995 | Siber et al. |
| 5,530,102 A | 6/1996 | Gristina et al. |
| 5,582,827 A | 12/1996 | Siber et al. |
| 5,599,539 A | 2/1997 | Carroll et al. |
| 5,601,823 A | 2/1997 | Williams et al. |
| 5,762,934 A | 6/1998 | Williams et al. |
| 5,773,000 A | 6/1998 | Bostwick et al. |

FOREIGN PATENT DOCUMENTS

| | | |
|---|---|---|
| WO | WO 94/13264 | 6/1994 |
| WO | WO 96/07430 | 3/1996 |
| WO | WO 96/12802 | 5/1996 |
| WO | WO 97/02836 | 1/1997 |

OTHER PUBLICATIONS

Mulligan et al 1993 (Clinical Infectious Diseases 16/SUPPL 4 S239–244).*

Johnson et al 1992 (J. Infectious Diseases: 166, 1287–94).*

Allo et al., "Prevention of Clindamycin–Induced Colitis in Hamsters by *Clostridium sordelli* Antitoxin," *Gastroenterology* 76:351–355 (1979).

Corthier et al., "Protection against Experimental Pseudomembranous Colitis in Gnotobiotic Mice by Use of Monoclonal Antibodies Against *Clostridium difficile* Toxin A," *Infection and Immunity* 59:1192–1195 (1991).

Fekety et al., "Diagnosis and Treatment of *Clostridium difficile* Colitis," *Journal of the American Medical Association* 269:71–75 (1993).

Fernie et al., "Active and Passive Immunization to Protect Against Antibiotic Associated Caecitis in Hamsters," *Dev. Biol. Stand* 53:325–332 (1983).

Johnston, "Antibody Responses to Clostridial Infection in Humans," *Clinical Infectious Diseases* 25:2 S173–177 (1997).

Kelly et al., "Anti–*Clostridium difficile* Bovine Immunoglobulin Concentrate Inhibits Cytotoxicity and Enterotoxicity of C. difficile Toxins," *AntiMicrobial Agents and Chemotherapy* 40:373–379 (1996).

Kim et al., "Immunization of Adult Hamsters against *Clostridium difficile*–Associated Ileocecitis and Transfer of Protection to Infant Hamsters," *Infection and Immunity* 55:2984–2992 (1987).

Kyne et al., "Prospects for a vaccine for *Clostridium difficile*," *BioDrugs* 10:173–181 (1998).

Leung et al., "Treatment with Intravenously Administered Gamma Globulin of Chronic Relapsing Colitis Induced by *Clostridium difficile* Toxin," *The Journal of Pediatrics* 188:633–637 (1991).

Libby et al., "Effects of the Two Toxins of *Clostridium difficile* and Immunological Comparison of the Toxins by Cross–Neutralization Studies," *Infection and Immunity* 36:822–829 (1982).

Libby et al., "Production of Antitoxins of Two Toxins of *Clostridium difficile* and immunological Comparison of the Toxins by Cross–Neutralization Studies," *Infection and Immunity* 35:374–376 (1982).

Lyerly et al., "Passive Immunization of Hamsters Against Disease Caused by *Clostridium Difficile* by use of Bovine Immunoglobulin G Concentrate," Infection and Immunity 59:2215–2218 (1991).

(List continued on next page.)

Primary Examiner—Nita Minnifield
Assistant Examiner—Padmavathi Baskar
(74) Attorney, Agent, or Firm—Clark & Elbing LLP

(57) ABSTRACT

The invention provides active and passive immunization methods for preventing and treating *Clostridium difficile* infection, which involve percutaneous administration of C. difficile toxin-neutralizing polyclonal immune globulin, C. difficile toxoids, or combinations thereof. Also provided by the invention are C. difficile toxoids, C. difficile toxin-neutralizing polyclonal immune globulin, and methods of identifying subjects that produce C. difficile toxin-neutralizing polyclonal immune globulin.

2 Claims, 6 Drawing Sheets

OTHER PUBLICATIONS

Lyerly et al., "Vaccination Against Lethal *Clostridium Difficile* Enterocolitis with a Nontoxic Recombinant Peptide of Toxin A," *Current Microbiology* 21:29–32 (1990).

Mitty et al., "*Clostridium difficile* Diarrhea: Pathogenesis, Epidemiology, and Treatment," *The Gastroenterologist* 2:61–69 (1994).

Salcedo et al., "Intravenous Immunoglobulin Therapy for Severe *Clostridium difficile* Colitis," *Gut* 41:366–370 (1997).

Torres et al., "*Clostridium difficile* Vaccine: Influence of Different Adjuvants and Routes of Immunization on Protective Immunity in Hamsters," *Vaccine Research* 5:149–162 (1996).

Torres et al., "Evaluation of Formalin–Inactivated *Clostridium difficile* Vaccines Administered by Parenteral and Mucosal Routes of Immunization in Hamsters," *Infection and Immunity* 63:4619–4627 (1995).

Warny et al., "Gamma Globulin Administration in Relapsing *Clostridium difficile*–Induced Pseudomembranous Colitis with Defective Response to Toxin A," *Acta Clinica Belgica* 50:36–39 (1995).

* cited by examiner

DAY (*ANIMALS IMMUNIZED)

* NO RESPONSE WAS DETECTED IN PLACEBO TREATED ANIMALS.

PASSIVE IMMUNIZATION AGAINST CLOSTRIDIUM DIFFICILE DISEASE

This application is a continuation of, and claims priority from, U.S. Ser. No. 09/176,076 filed on Oct. 20, 1997 (now U.S. Pat. No. 6,214,341), which claims priority from U.S. Ser. No. 60/062,522, filed Oct. 20, 1997.

BACKGROUND OF THE INVENTION

This invention relates to methods and compositions for preventing and treating *Clostridium difficile* disease.

*Clostridium difficile*, a toxin-producing gram positive bacterium, invades the intestinal tracts of patients whose normal intestinal flora is suppressed due to treatment with broad spectrum antibiotics. The bacterial toxins cause varying degrees of damage to the large intestinal (i.e., colonic) epithelium, and cause a spectrum of illnesses, ranging from mild diarrhea to severe colitis. Because antibiotic treatment induces the onset of *C. difficile* disease, the associated syndromes are named antibiotic-associated diarrhea and colitis (LaMont, Bacterial Infections of the Colon, Textbook of Gastroenterology, second edition, 1897–1903, 1995).

Three clinical syndromes caused by *C. difficile* are recognized, based on severity of the infection. The most severe form is pseudomembranous colitis (PMC), which is characterized by profuse diarrhea, abdominal pain, systemic signs of illness, and a distinctive endoscopic appearance of the colon. The case-fatality rate of PMC may be as high as 10%. Antibiotic-associated colitis (AAC) is also characterized by profuse diarrhea, abdominal pain and tenderness, systemic signs (e.g., fever), and leukocytosis. Intestinal injury in AAC is less than in PMC, the characteristic endoscopic appearance of the colon in PMC is absent, and mortality is low. Finally, antibiotic-associated diarrhea (AAD) is the mildest syndrome caused by *C. difficile*, and is characterized by mild-moderate diarrhea, lacking both large intestinal inflammation (as characterized, e.g., by abdominal pain, tenderness) and systemic signs of infection (e.g., fever). These three distinct syndromes occur in an increasing order of frequency. That is, PMC occurs less frequently than AAC, and AAD is the most frequent clinical presentation of *C. difficile* disease.

The populations affected by *C. difficile* are principally hospitalized, elderly patients and nursing home residents who have received broad spectrum antibiotics. Old age, length of hospital stay, underlying illness, and use of antibiotic therapy are recognized risk factors for *C. difficile* infection (McFarland et al., J. Infect. Dis. 162:678–684, 1990; Bennett, Aging, Immunity, and Infection, 216–229, 1994). A frequent complication of *C. difficile* infection is relapsing disease, which occurs in up to 20% of all subjects who recover from *C. difficile* disease. Relapse may be characterized clinically as AAD, AAC, or PMC. There are no specific risk factors or predisposing factors for relapse, but patients who relapse once are more likely to relapse again.

*C. difficile* produces two exotoxins, Toxin A and Toxin B, which mediate the disease process caused by *C. difficile*. Toxin A and Toxin B are large (~300 kDa) extracellular proteins, the active forms of which are believed to be homodimers. The toxins are stably expressed in approximately equivalent amounts from a single chromosomal locus (Mitty et al., The Gastroenterologist 2:61–69, 1994). The toxins have nearly 50% amino acid sequence homology, but are immunologically distinct. The 100 kDa carboxyl-termini of the two toxins contain repetitive oligopeptides, and are involved in carbohydrate receptor binding in vivo. Receptor specificity is believed to mediate tissue and host specificity of toxin action. This region is also more immunogenic than the amino terminus. The amino terminal 200 kDa region contains the enzymatic domain, which is believed to glycosylate the GTP binding proteins Rho, Rac, and Cdc42, thereby preventing their phosphorylation, and leading to a loss of actin polymerization and cytoskeletal integrity (Eichel-Streiber, Trends Micro. 4:375–382, 1996). As a result of the cytoskeletal changes, tight junctions between epithelial cells are lost. The epithelial damage in conjunction with local inflammatory events causes fluid exudation into the gut, manifested as diarrhea (Mitty et al., supra).

By virtue of their inhibition of cytoskeleton structure, both toxins cause the rounding of cells in tissue culture at very low concentrations. The dose that causes morphologic change in 50% of cells ($MC_{50}$) for Toxin A on IMR90 cells is 0.4 ng/ml and for Toxin B is 3.5 pg/ml (Torres et al., Infect. & Immun. 63:4619–4727, 1995). Toxin A is an enterotoxin that causes fluid accumulation in ligated animal intestinal loops. Although Toxin B does not induce fluid secretion in animal intestinal loops, both it and Toxin A elicit inflammatory changes in vivo and in vitro (Mitty et al., supra). Both toxins are lethal to animals when administered systemically.

SUMMARY OF THE INVENTION

The invention provides methods of treating *Clostridium difficile* disease in human patients. These methods involve percutaneously (e.g., intramuscularly, intravenously, or intraperitoneally) administering to a patient human *C. difficile* polyclonal immune globulin that neutralizes both Toxin A and Toxin B (hereinafter "immune globulin") (e.g., 0.01–100 mg/kg body weight). These methods can also include percutaneous administration of a clostridial toxin or toxoid to a patient, to stimulate an anti-*C. difficile* immune response in the patient. When administered as treatment in affected individuals, the injected immune globulin will also prevent relapse.

Also included in the invention are methods of preventing *C. difficile* disease in human patients. In these methods, a toxin-neutralizing antibody to a *C. difficile* toxin or toxoid (e.g., a *C. difficile* polyclonal immune globulin (e.g., 0.01–100 mg/kg body weight)) is percutaneously (e.g., intramuscularly, intravenously, or intraperitoneally) administered to a human subject at risk of becoming infected with *C. difficile*. The *C. difficile* immune globulin used in these methods can be produced, e.g., in a human. These methods can also include percutaneous administration of a clostridial toxin or toxoid containing Toxin A and Toxin B epitopes to the patient.

The invention also provides methods of preventing or treating intestinal clostridial disease in human patients, which involve percutaneously administering a clostridial (e.g., *C. difficile*) toxin or toxoid to a patient, in the presence or absence of an adjuvant, such as alum. An additional method included in the invention involves administering *C. difficile* immune globulin, as described above, to rapidly treat or protect a patient, while simultaneously administering toxoid for long-term, active protection by means of stimulation of the patient's immune system.

All of the prophylactic and therapeutic methods described above can, in conjunction with percutaneous administration, involve mucosal administration, such as oral or rectal administration.

Also included in the invention are methods of producing *C. difficile* toxoid. These methods involve providing *C.*

*difficile* bacteria; culturing the bacteria in media containing suitable animal products (e.g., casein products) to generate a culture; co-purifying clostridial Toxin A and clostridial Toxin B from the culture to generate a mixture of co-purified Toxin A and Toxin B; and inactivating the co-purified Toxin A and Toxin B by incubation in formaldehyde at a temperature of about 25° C. or less (e.g., 15° C. or less, or 5° C. or less) to generate the clostridial toxoid. The co-purified Toxin A and Toxin B can be present in the mixture at a ratio in the range of 0.1:1 to 10:1, for example, 2:1. The invention also includes a *C. difficile* toxoid produced by this method, and a vaccine composition containing this toxoid and 0.012–0.020% formaldehyde. Optionally, this composition can contain an adjuvant, such as alum.

The invention also provides methods of producing human, toxin-neutralizing *C. difficile* immune globulin. In these methods, *C. difficile* toxin or toxoid containing, e.g., Toxin A and/or Toxin B, is administered to a human, and *C. difficile* immune globulin is isolated from the human. *C. difficile* immune globulin produced using these methods is also included in the invention.

Also included in the invention are methods of identifying a human producing a *C. difficile* immune globulin. These methods involve obtaining a blood sample from a human vaccinated with a *C. difficile* toxoid; determining the level of antibodies to *C. difficile* Toxins A and B in the blood sample by an enzyme-linked immunosorbent assay (ELISA); and determining the level of in vitro cytotoxicity neutralization activity against *C. difficile* Toxins A and B in the blood sample. Detection of increased levels of antibodies to *C. difficile* Toxins A and B in the blood sample, and detection of in vitro cytotoxicity neutralization activity against *C. difficile* Toxins A and B in the blood sample, indicate identification of a human producing a *C. difficile* immune globulin. In addition to humans that have been vaccinated with a *C. difficile* toxoid, this method can be carried out with unvaccinated humans to identify good candidates for vaccination.

The term "*C. difficile* immune globulin," is used herein to describe polyclonal hyperimmune serum raised in subjects (e.g., human volunteers) vaccinated with *C. difficile* toxoids. The immune globulin contains antibodies that neutralize cytotoxicity and in vivo effects of Toxin A and Toxin B.

The term "*C. difficile* toxoid" is used to describe a *C. difficile* toxin (Toxin A or Toxin B) or a mixture of *C. difficile* toxins that have been partially or completely inactivated, for example, by chemical (e.g., formaldehyde) treatment. A toxin is said to be "inactivated" if it has less toxicity (e.g., 100%, 99%, 95%, 90%, 80%, 75%, 60%, 50%, 25%, or 10% less toxicity) than untreated toxin, as measured, for example, by an in vitro cytotoxicity assay or by animal toxicity. Other chemical means for inactivating toxins can be used including, for example, peroxide or glutaraldehyde treatment. Toxoids can also be generated by genetic changes that result in toxin inactivation.

The invention provides several advantages. For example, treatment using the methods of the invention specifically results in inactivation of *C. difficile* bacterial toxins, without affecting normal intestinal flora. Both *C. difficile* Toxin A and Toxin B are involved in human disease, and the immunotherapy methods of the invention can be used to target both of these molecules. Recovery using immunotherapy is more rapid than antimicrobial therapy, which targets vegetative bacteria, rather than directing toxin neutralization. The specific neutralization of toxin activity has the advantage of specifically and rapidly inactivating the cause of tissue damage. In addition, a single dose of *C. difficile* immune globulin, administered percutaneously (e.g., intramuscularly, intravenously, or intraperitoneally), can be used in the methods of the invention, rather than the repeating dosing required for oral administration (Lyerly et al., Infect. & Immun. 59:2215–2218, 1991). The overall dose of *C. difficile* immune globulin administered percutaneously is lower than the dose required in oral methods, due to the longer half life of injected antibodies, compared to orally administered antibodies (hours vs. weeks or months). Specific antibody therapy also permits continuation of treatment of underlying conditions with antibiotics, which may otherwise have to be withdrawn to permit reconstitution of the intestinal flora and recovery from *C. difficile* infection. Also, treatment using the methods of the invention prevents the emergence of antibiotic-resistant bacteria. *C. difficile* disease has been traditionally treated with vancomycin and metronidizole, and use of vancomycin has led to the emergence of vancomycin-resistant enterococcus. Similar problems may be arising from metronidizole treatment. Finally, *C. difficile* is cultured in the methods of the invention in medium that lacks complex animal products, such as nervous system products, e.g., the animal products in Brain Heart Infusion medium. Media containing such complex animal products have been found to contain the bovine spongiform encephalopathy (BSE) prion. Thus, in not using such medium, the invention provides safety against infection by such agents.

Other features and advantages of the invention will be apparent from the following detailed description, the drawings, and the claims.

DETAILED DESCRIPTION

Figure 1:
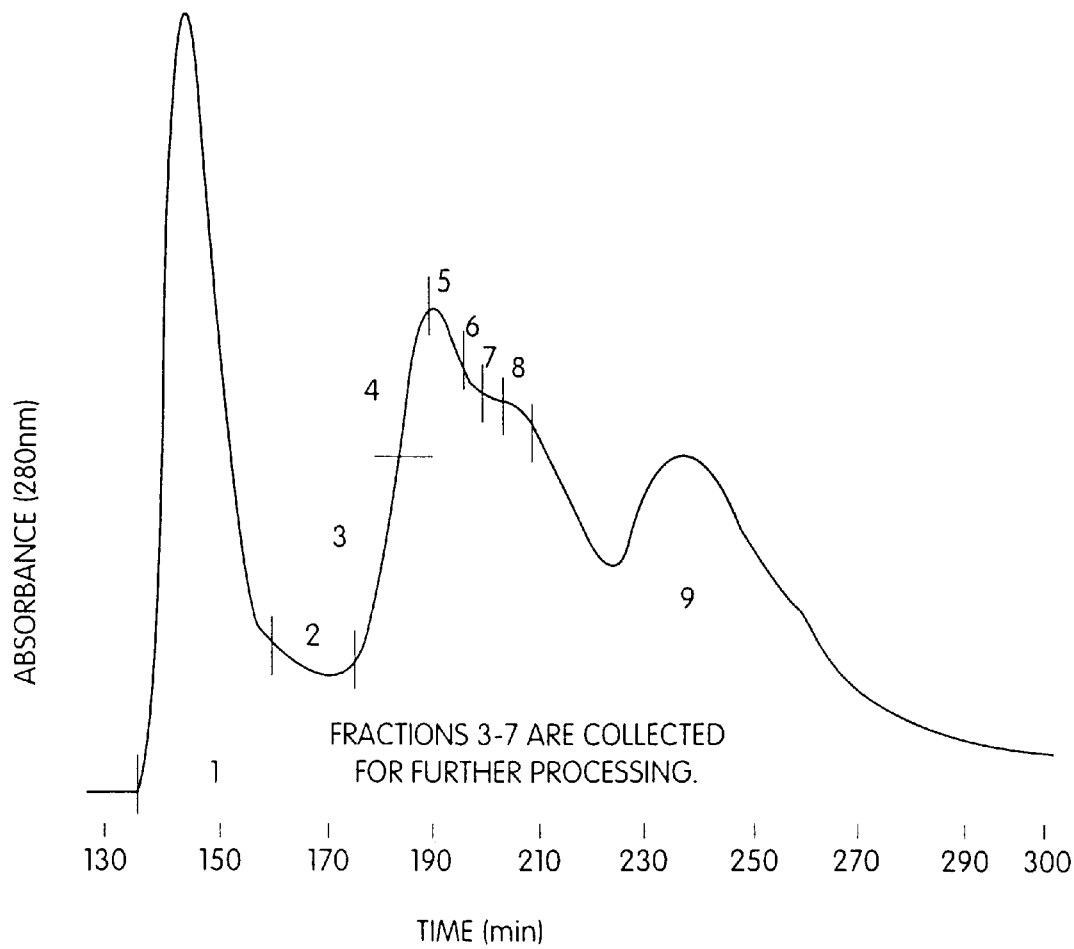
FIG. 1 is a chromatogram tracing of the elution profile of a *C. difficile* ammonium sulfate precipitate from an Sephacryl S-300 column.

The invention provides methods and compositions for preventing and treating *C. difficile* disease in mammals, such as humans. The methods include passive and active immunization approaches, which involve percutaneous (e.g., intramuscular, intravenous, or intraperitoneal) administration of antibodies (e.g., toxin-neutralizing polyclonal immune globulin) to *C. difficile* toxoids, *C. difficile* toxoids themselves, or combinations thereof. The invention also includes *C. difficile* toxoids, vaccine compositions containing *C. difficile* toxoids, methods of producing *C. difficile* toxin-neutralizing polyclonal immune globulin, substantially purified *C. difficile* toxin-neutralizing polyclonal immune globulin, and methods of identifying donors of *C. difficile* toxin-neutralizing polyclonal immune globulin. These methods and compositions are described further, as follows.

The prophylactic and therapeutic methods of the invention involve vaccination with *C. difficile* toxoids, whether in carrying out the treatment itself or in the production of *C. difficile* immune globulin for subsequent use in passive immunization. *C. difficile* toxoids are produced by purification of toxins (Toxin A, Toxin B, or, preferably, a combination of Toxin A and Toxin B) from *C. difficile* cultures, and inactivation of the toxins by chemical, e.g., formaldehyde (see below), glutaraldehyde, peroxide, or oxygen, treatment (see, e.g., Relyveld et al., Methods in Enzymology 93:24, 1983; Woodrow and Levine, eds., *New Generation Vaccines,* Marcel Dekker, Inc., New York, 1990). Alternatively, mutant *C. difficile* toxins that lack or have reduced toxicity can be produced using recombinant methods. Methods for making toxoids by genetic methods are well known in the art (see, e.g., U.S. Pat. Nos. 5,085,862; 5,221,618; 5,244,657; 5,332,583; 5,358,868; and 5,433,945). For example, deletion mutations that remove the amino terminal, enzymatic region of the toxin can be made. Deletion or point mutations can also be made in the toxin active site. In addition, deletion or point mutations can be made that prevent receptor or carbohydrate binding.

Vaccine compositions containing *C. difficile* toxoids can be prepared for administration by suspension of the toxoids in a pharmaceutically acceptable diluent (e.g., physiological saline) or by association of the toxoids with a pharmaceutically acceptable carrier. The toxoids can be administered in the presence or absence of an adjuvant, in amounts that can be determined by one skilled in the art. Adjuvants that can be used in the invention include aluminum compounds, such as aluminum hydroxide, aluminum phosphate, and aluminum hydroxy phosphate. The antigen can be precipitated with, or adsorbed onto, the aluminum compound using standard methods. As a specific example, alum (e.g., Rehydragel LV®, Reheis, Inc., Berkeley Heights, N.J.; up to 2 mg AlOH/dose, e.g., about 1.5 mg AlOH/dose) can be used. Additional adjuvants that can be used include RIBI (ImmunoChem, Hamilton, Mont.), QS21 (Aquila), Bay (Bayer), and Polyphosphazene (Virus Research Institute, Cambridge, Mass.; WO 95/2415).

The vaccine compositions of the invention can be administered by the percutaneous (e.g., intramuscular, intravenous, or intraperitoneal) route in amounts and in regimens determined to be appropriate by one skilled in the art. For example, 100 ng–500 μg, 1–250 μg, or 10–100 μg toxoid can be administered. For the purposes of prophylaxis or therapy, the vaccine can be administered, for example, 1, 2, 3, or 4 times. Preferably, only 1 or 2 administrations are carried out. When multiple doses are administered, the doses can be separated from one another by, for example, one week to a month. For the purposes of stimulating donors of *C. difficile* immune globulin, a higher number of doses can be administered. For example, up to 6 doses can be administered, separated from each other by, e.g., one week to a month.

When vaccination is performed to generate *C. difficile* polyclonal immune globulin, e.g., human *C. difficile* polyclonal immune globulin, serum samples from the immunized donors are first monitored for the presence of *C. difficile* Toxin A and Toxin B by enzyme-linked immunosorbent assay (ELISA) analysis. Briefly, ELISA plates are coated with carbonate/bicarbonate, pH 8.5, and 1 μg/ml protein (purified Toxin A or Toxin B), and incubated at 4° C. overnight. The wells are contacted with serum samples diluted in phosphate-buffered saline (PBS), washed, and contacted with an anti-human antibody coupled to a detectable label, such as alkaline phosphatase. Detection of a signal of greater than two times over background is considered positive. Signal is detected by optical density measurement at 405 nm.

Samples that test positive in the ELISA assay are then tested in a toxin neutralization assay. Briefly, serum samples (100 μl) are serially diluted two-fold in MEM, and are pre-incubated with an equal volume of Toxin A containing 10 $MC_{50}$ for 1 hour at 37° C. The Toxin A concentration is standardized for challenge of the cells. For example, ten times the concentration that affects 50% of the cells is used for challenge. The range used for Toxin A is 10–100 ng. Toxin A/serum mixtures (100 μl) are then added to confluent IMR90 cell monolayers (American Type Culture Collection (ATCC, 10801 University Boulevard. Manassas, Md. 29110-2209); Torres et al., supra). The overlaid cells are incubated for 16–18 hours at 37° C., and are then scored for cytotoxicity. If at least 50% of the cells are protected from rounding, the sera is rated "protective." The potency test for Toxin B is performed by the same procedures described above for Toxin A, except that the serum samples are Preincubated with Toxin B prior to determination of cytotoxicity in the IMR90 cell assay. The amount of Toxin B that has an effect on 50% of IMR90 cells is 10–100 μg.

The screening methods described above can also be used to identify subjects that have not been vaccinated with *C. difficile* toxoids, but have higher than normal serum levels of antibodies against *C. difficile* toxins. These subjects are good candidates for vaccination with the toxoids, for production of *C. difficile* immune globulin.

Once an acceptable donor is identified, immune globulin is obtained from the donor using standard plasmapheresis methods. The immune globulin is purified using standard methods, such as Cohn cold-ethanol fractionation, or standard chromatography methods, such as sizing column chromatography or antibody affinity chromatography (e.g., using Protein A). Up to two times per week, whole blood (500 ml–1 L) is obtained from donors, plasma is isolated by centrifugation, and cells are returned to the donors. Preferably, the purified sample contains all or predominantly IgG, but mixtures containing, e.g., IgG, IgA, and IgM, can also be used in the invention.

The *C. difficile* immune globulin, prepared as described above, can be percutaneously (e.g., intramuscularly, intravenously, or intraperitoneally) administered to patients that have, or are at risk of developing, *C. difficile* infection. These patient populations include, for example, patients that have received broad spectrum antibiotics, such as hospitalized elderly patients, nursing home residents, chronically ill patients, cancer patients, AIDS patients, patients in intensive care units, and patients receiving dialysis treatment. The *C. difficile* immune globulin is administered in amounts ranging from 100 μg/kg-100 mg/kg, or 1–50 mg/kg, for example, about 15 mg/kg, depending on donor titer: the higher the neutralization titer of the immune globulin, the lower the amount is that needs to be administered. The immune globulin can be administered in, e.g., one or two doses. For example, in the case of therapeutic passive immunization, an initial dose can be administered for treatment and a second dose can be administered to prevent relapse.

The methods and compositions of the invention, as well as experimental evidence supporting the invention, are described in further detail, as follows.

Vaccine Production

Overview

C. difficile Toxin A and Toxin B are produced in anaerobic cultures of C. difficile grown in culture bottles (10–20 L). Master and working cell banks of C. difficile were manufactured from a lyophilized research cell bank prepared at the ATCC from C. difficile strain ATCC 43255. For vaccine production, toxins are produced by C. difficile cultures grown in dialysis sacs, suspended in growth medium. Multiple sac cultures are pooled, and viable C. difficile and spores are removed by centrifugation, followed by submicron filtration. The resulting filtrate is concentrated and diafiltered, the toxins are precipitated at 4° C. with 60% saturated ammonium sulfate, and pellets are stored frozen. The ammonium sulfate pellets are re-dissolved in phosphate buffer, and applied to an S-300 Sephacryl size-exclusion column. The peak containing Toxin A and Toxin B is collected and concentrated (50–60% toxin, with a ratio of Toxin A to Toxin B of 2:1). The toxin preparation is then inactivated for 18 days with 4.25 mg/ml formaldehyde at 4° C.–6° C. in a solution containing 4.25 mg/ml lysine. After inactivation, the formaldehyde concentration is reduced by diafiltration to 0.016% for use as a stabilizer. Final product, at a concentration of 2.5 mg/ml, is filled into glass vials at a fill volume of 0.6 ml.

The current process yields 15–20 mg/L, or 150–200 doses, of toxoid. Lot release testing assays of identity, potency, and safety have all been established on preclinical lots. GMP Master and Production cell banks have been generated, qualified, and stored in a stable condition. C. difficile toxoid vaccine preparation is described in further detail, as follows.

Master and Working Cell Banks

A research seed was prepared and lyophilized under contract by the ATCC by their standard methods using an ampule of the type strain ATCC 43255. Oxoid Reinforced Clostridial Medium (RCM) was used to grow the seed stock (Oxoid Ltd., Hampshire, England). The bovine-derived materials in media were obtained in Australia, New Zealand, Holland, and the USA from healthy animals used for human consumption. Cultures were stabilized in RCM using 5% dextran and trehalose as preservatives.

Preparation of C. difficile Master Cell Bank (MCB) and Working Cell Bank (WCB)

The MCB of C. difficile was prepared by resuspending and incubating a lyophilized vial of the research seed stock in RCM (the same lot used by the ATCC), followed by two expansions in Tryptone (0.48%)-Yeast Extract (0.24%)-Mannitol (0.1%) (TYM) medium. Glycerol was added as cryopreservative and 250 aliquots of 1 ml each were snap frozen and stored in liquid nitrogen. The working cell bank was prepared in a similar fashion using a vial of the MCB as inoculum.

Cell Bank Testing

The master and working cell banks were tested for viability, purity, identity, and toxin expression. Viability was demonstrated by growth on both solid and liquid medium. Purity was tested by gram stain and colony morphology under anaerobic culture, and by the absence of aerobic growth. C. difficile identity was demonstrated by gas chromatography fatty acid analysis and by clinical anaerobic identity testing. Toxin expression and identity were confirmed by culturing the cell banks in dialysis sacs and testing the culture for expression of both toxins by crossed immunoelectrophoresis. Toxin A expression and identity were also confirmed by ELISA. Toxin B expression was confirmed by testing for cytotoxicity and specific neutralization of cytotoxicity. Toxin expression was measured in parallel with ATCC 43255 standards and was shown to be comparable.

Culture and Toxin Expression

Toxins are produced in anaerobic cultures of C. difficile grown in dialysis sacs (13–14,000 MW cutoff) and suspended in a media containing a nitrogen source (e.g., tryptone in a concentration of 1–100 g/L, 5–20 g/L, or 12 g/L), yeast extract (1–100 g/L, 15–35 g/L, or 24 g/L), phosphate buffer, a carbon source (e.g., mannitol (1–50 g/L, e.g., 8 g/L), glucose, glycerol (1–50 g/L, e.g., 4 g/L), or mannitol+glycerol (e.g., in the amounts set forth above)). Production is initiated by expanding a vial of the working cell bank in a small static culture and using aliquots of the culture to inoculate dialysis sacs. After growth at 37° C. for approximately 5 days, material in the sacs is harvested. The harvested product is centrifuged and filtered (0.5 μm followed by 0.2 μm) to remove vegetative cells and spores. The filtrate is washed, concentrated, and precipitated with ammonium sulfate.

Preparation of Culture Units

A culture unit consists of an 8 L or 16 L spinner flask, with two sidearm ports, a dialysis sac, and a 1 L or 2 L flask of phosphate buffer. Up to twenty-five 8 L or 16 L units are inoculated for each production run. The culture unit is prepared by dissolving media in a spinner flask, suspending the dialysis sac between the sidearm ports, capping the ends of the ports, and attaching a flask of 100 mM phosphate buffer to one port. The entire unit is autoclaved for media sterilization and creation of anaerobiasis. After cooling to below 50° C., the phosphate buffer is pumped into the dialysis sac and the unit is equilibrated overnight at 37° C., prior to inoculation during which growth nutrients diffuse into the dialysis sac, establishing conditions suitable for bacterial growth.

Inoculation and Culture

A vial of the working cell bank is thawed and used to inoculate 50 ml of anaerobic TY starter medium (tryptone (0.48%) and yeast extract (0.24%)). The flask is placed in an anaerobic chamber at 37° C. for 14–16 hours. Approximately 2 ml of inoculum in an appropriate volume of diluent is added to each dialysis sac. The culture units are then returned to the incubator and left undisturbed for 5 days. Anaerobiasis is maintained after autoclaving by preventing unnecessary agitation.

Harvest, Filtration, and Precipitation

Following incubation, culture units are removed from the incubator, and the contents of the dialysis sacs are pumped out, pooled, and tested for culture purity and identity. Viable C. difficile organisms and spores are removed by centrifugation, followed by filtration through a 0.5 μm pre-filter and then through a 0.2 μm sterilizing filter. The filtrate is tested for Toxin A and Toxin B concentration and sterility, and concentrated 10× by ultrafiltration with a 30,000 MW cutoff hollow fiber cartridge. The filtrate is washed with 25 mM Tris, pH 7.5, resulting in a reduction in low molecular weight media components. Filtered, saturated ammonium sulfate solution is added to the concentrate to give a final solution of 60% saturation. The solution is incubated at 4° C. for 48 hours or longer, the toxin-containing precipitate is harvested by centrifugation, and the supernatant decanted. The ammonium sulfate pellet is stored frozen at −10° C. or colder until processed further.

Purification and Inactivation

The pellet is thawed by mixing with 100 mM phosphate buffer, pH 7.4, at room temperature. Solubilized toxin is clarified by centrifugation and filtered using a 0.45 μm filter. Clarified material is then fractionated on a Sephacryl S-300 High Resolution (Pharmacia Biotechnology) gel filtration column. A typical chromatographic profile is shown in FIG. 1. The toxin peak is collected and concentrated to 5.0±0.5 mg/ml. Collection begins with the ascending limb of the toxin peak and continues to the inflection point on the descending limb, as determined by visual inspection of the chromatogram.

After purification, the toxin solution is inactivated for 18 days at 4–6° C. using 4.25 mg/ml of formaldehyde. The inactivation is carried out at pH 7.0±0.2 in 100 mM phosphate buffer containing 4.25 mg/ml lysine hydrochloride. The inactivation period is set to exceed three times the period needed for complete elimination of lethality in mice. Thus, by day 6 of inactivation, intraperitoneal inoculation with 0.5 mg of toxoid produces no lethality or weight change in mice. This corresponds to a reduction in the cytotoxicity titer in IMR90 cells of approximately 6 $\log_{10}$. Following 18 days of inactivation, biological activity is typically reduced another 2 to 3 orders of magnitude, as judged by effects on IMR90 cells, for a total extent of inactivation of 8 to 9 $\log_{10}$.

Following 18 days of inactivation, the inactivated toxin is buffer-exchanged in 50 mM phosphate, 100 mM NaCl, pH 7.4, reducing the formaldehyde concentration to 0.16±0.04 mg/ml. The soluble, inactivated toxin at 2.5 mg/ml is sterile filtered and filled into 2 ml Type I borosilicate glass vials with gray butyl rubber stoppers.

Studies Supporting Conditions of Inactivation and Formulation

Extensive studies were conducted to establish optimal conditions for toxin inactivation with formaldehyde. To monitor loss of biological activity, these studies utilized the IMR90 tissue culture system, which is a highly sensitive indicator of biological activity of *C. difficile* toxin (Torres et al., supra). Parameters studied included concentration of formaldehyde and toxin, buffer composition, pH, time, temperature, and effect of added L-lysine, designed to facilitate full toxoiding (Table 1).

TABLE 1

Parameters Tested

| Parameters | Range tested |
| --- | --- |
| pH | 6.5; 7.0; 7.4; 8.0 |
| Temperature (° C.) | 5; 14; 28; 37 |
| Toxin concentration (mg/ml) | 1; 5 |
| Formaldehyde concentration (mg/ml) | 0.5; 1.0; 2.0; 2.5; 4.25; 10; 15; 20 |
| Lysine HCl concentration (mg/ml) | 1; 2; 4.25 |

Figure 2:
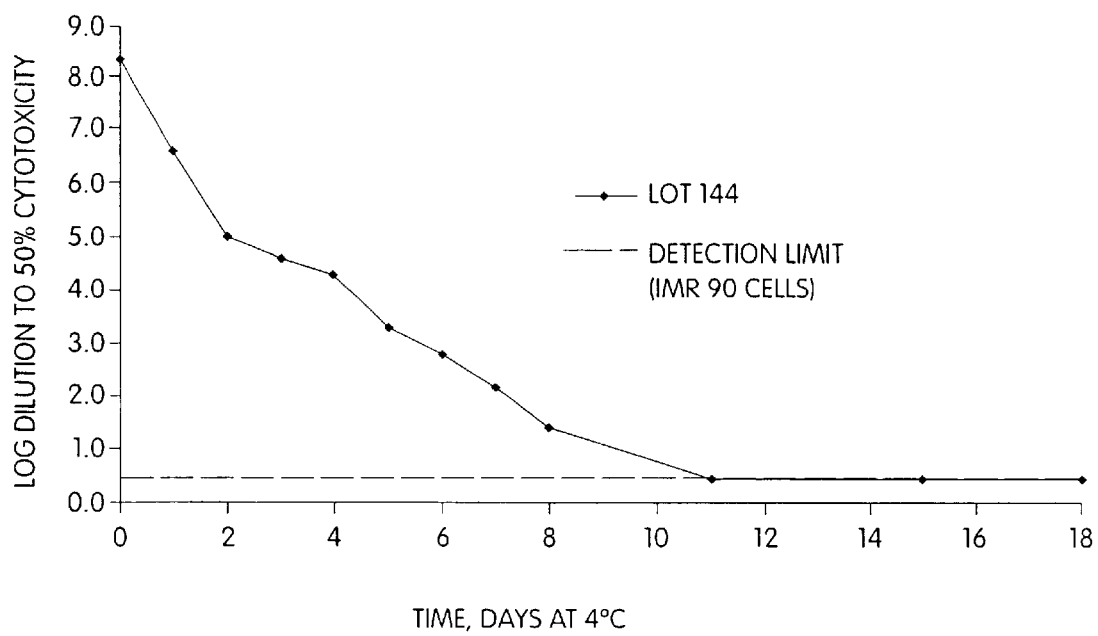
FIG. 2 is a graph showing the inactivation kinetics of *C. difficile* toxin lot 144.
Figure 3:
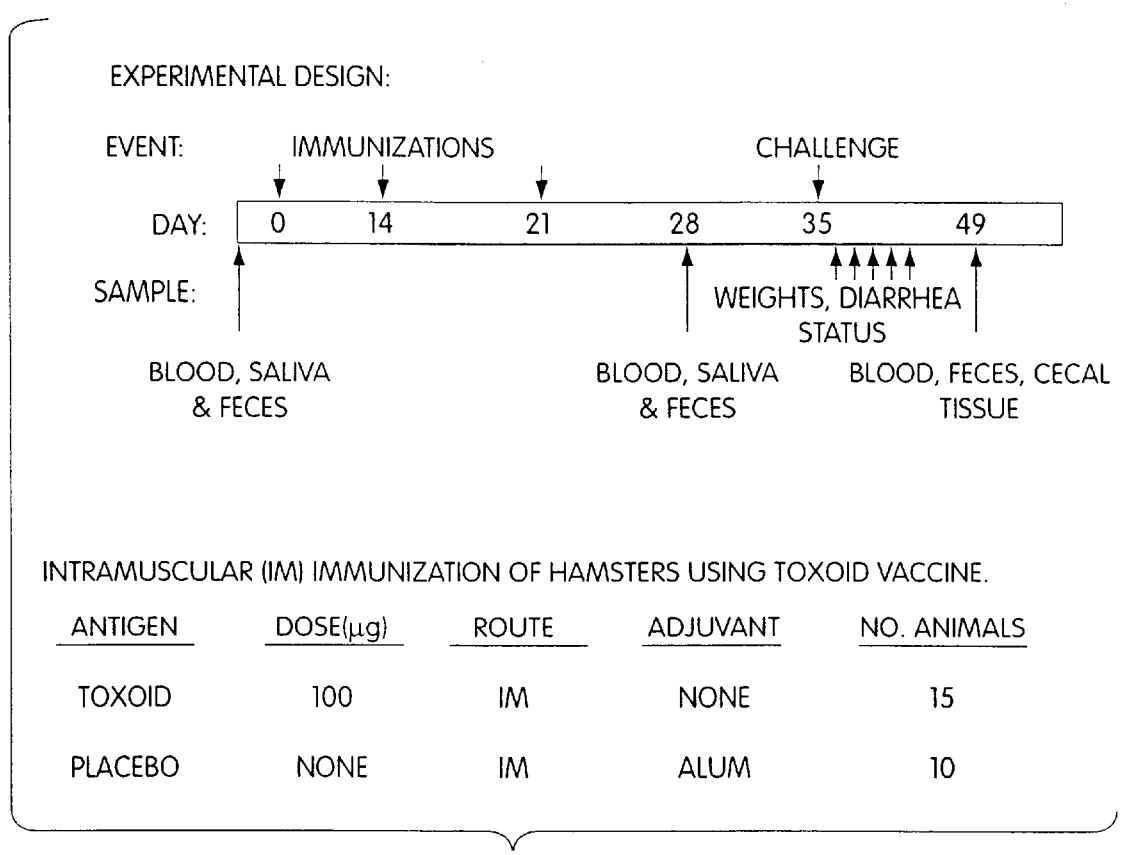
FIG. 3 is a schematic representation of a schedule for active immunization of hamsters with *C. difficile* toxoid vaccine for protection from challenge after immunization.
Figure 4:
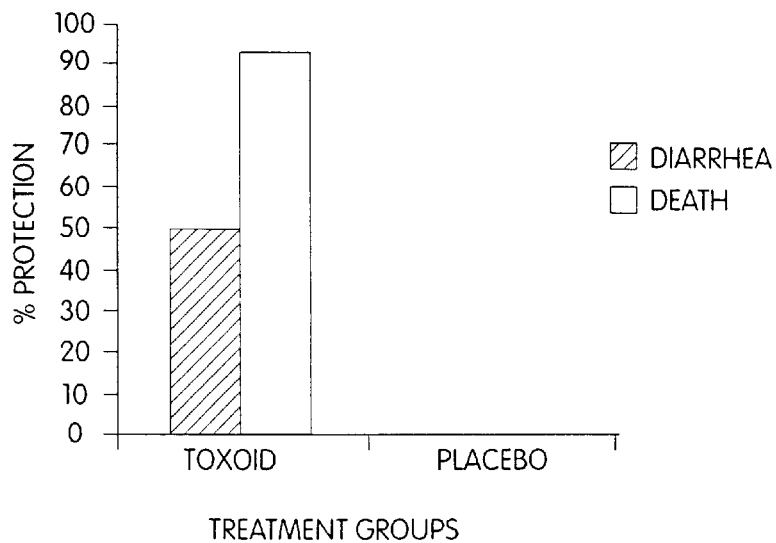
FIG. 4 is a graph showing that hamsters immunized intramuscularly with toxoid vaccine are protected from death and diarrhea after *C. difficile* challenge.
Figure 5:
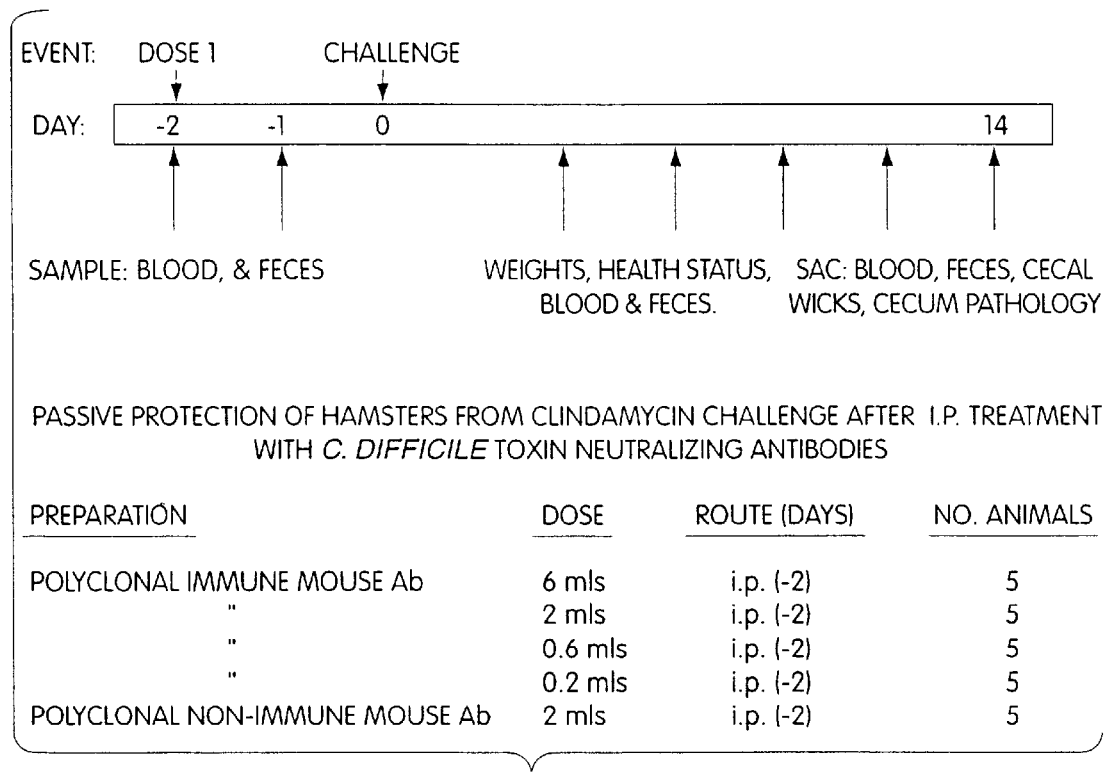
FIG. 5 is a schematic representation of a schedule for passive immunization of hamsters with *C. difficile* toxin-neutralizing antibodies.
Figure 6:
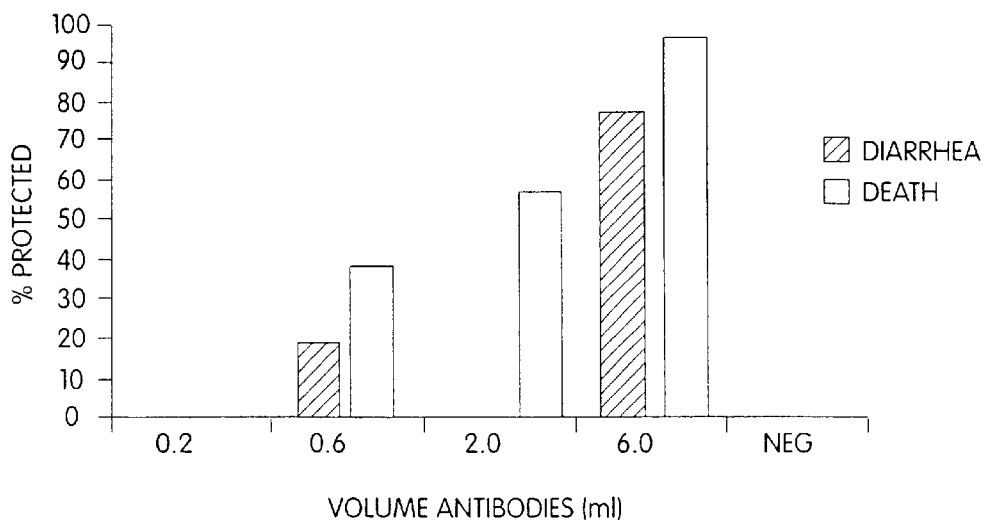
FIG. 6 is a graph showing that hamsters treated intraperitoneally with toxin-neutralizing antibodies are protected from death and diarrhea after *C. difficile* challenge.

In general, *C. difficile* toxins were very sensitive to inactivation at 37° C. under all conditions, with inactivation occurring extremely rapidly (e.g., loss of 7 $\log_{10}$ of activity in 8 hours). Therefore, to maximize control and reproducibility of the inactivation, we elected to inactivate at 4° C. Toxoids inactivated at 4° C. induced higher antibody titers than toxoids inactivated with formaldehyde at 37° C. Under the specified conditions chosen, complete loss of detectable in vivo biological activity occurs within 6 days of inactivation, corresponding to a loss of approximately 5–6 $\log_{10}$ in vitro. To provide a sufficient margin of safety, inactivation is continued for an additional 12 days, during which an additional 2–3 $\log_{10}$ of cytotoxicity are lost. At the end of the inactivation period, activity in the cell culture system is just barely detectable, at the threshold of detectability. Kinetics for a typical inactivation are shown in FIG. 2.

Low concentrations of formalin are included in the formulation of the vaccine to prevent toxoid reversion. Reversion was detected, despite Lys incorporation into the activation site, which is known to reduce reversion with other toxins (Relyveld, Prog. Immunobiol. Stand. 3:258, 1969). The choice of formulation was based on numerous studies undertaken to determine the stability of the toxoid, including the possibility of reversion, under various conditions. In general, the toxoid was stable at 4° C., with or without low concentrations of residual formalin. In the absence of residual formalin, partial reversion occurred at higher temperatures (28–37° C.), with the toxoid regaining detectable biological activity over days to weeks (Table 2).

TABLE 2

Partial Reversion of *C. difficile* Toxoid in Absence of Formalin

| Time of Incubation | $MC_{50}$ (IMR90 cell culture assay) | | |
| --- | --- | --- | --- |
| 37° C. (Days) | Lot 133A | Lot 135A | Lot 144A |
| 0 | 0.2 mg/ml* | 0.2 mg/ml* | 0.41 mg/ml |
| 7–8 | 0.10 mg/ml | 0.13 mg/ml | 0.2 mg/ml |
| 14 | 0.11 mg/ml | 0.13 mg/ml | 0.025 mg/ml |
| 35 | 0.052 mg/ml | 0.064 mg/ml | Not determined |
| 63 | 0.014 mg/ml | 0.017 mg/ml | Not determined |

*Estimated data

As noted, only partial reversion has been detected, even after exposure to optimal conditions for reversion (37° C.) for extended periods (over two months). After this time, approximately 5 $\log_{10}$ has been regained of the 8–9 $\log_{10}$ originally inactivated.

Reversion was completely prevented at all temperatures by inclusion of formalin at concentrations of 0.010% or higher (Table 3). Therefore, specifications for the formulated toxoid vaccine have been set to ensure a formalin concentration of 0.012–0.020%.

TABLE 3

Prevention of Reversion by Low Concentrations of Formalin

| | Lot 133B | | | |
| --- | --- | --- | --- | --- |
| Time of | $MC_{50}$ (mg/ml, IMR90 cell culture assay) | | | |
| Incubation (Days) | No formaldehyde | Formaldehyde 0.05 mg/ml | Formaldehyde 0.10 mg/ml | Formaldehyde 0.15 mg/ml |
| 0 | 0.33 | 0.20 | 0.11 | 0.11 |
| 4 | 0.00028 | 0.025 | 0.09 | 0.11 |
| 7 | 0.00028 | — | — | — |
| 14 | 0.000095 | 0.00028 | 0.12 | 0.053 |
| 28 | 0.00029 | 0.00029 | 0.12 | 0.12 |
| 56 | 0.00029 | 0.00029 | 0.12 | 0.12 |

Characterization of *C. difficile* Toxin (prior to inactivation)

Studies were undertaken to characterize the partially purified toxin preparation following size-exclusion chromatography, prior to formaldehyde treatment. Toxin A and Toxin B are not well separated in Tris-Glycine reducing SDS-PAGE. However, total toxin (Toxin A and Toxin B) can be estimated by densitometric scanning of Coomassie stained, Tris-Glycine reducing SDS-PAGE gels. Total toxin accounts for 50–60% of total protein. Immunoblots of these reducing gels show a major anti-Toxin A reactive band and a major and several minor anti-Toxin B reactive bands.

We have undertaken identification of the major impurities in the vaccine. SDS-PAGE gels were overloaded with purified bulk toxin and the proteins were separated under reducing SDS-PAGE conditions. The gel was cut just below the 244 kDa pre-stained marker to cutoff the toxin band. The proteins below the toxin band were then transferred to a PVDF membrane and subjected to amino acid sequencing for homology comparison to sequence databases. From N-terminal sequencing, 18–25 cycles, we have identified the ~35 kDa impurity as *C. difficile* 3-hydroxy butryl CoA dehydrogenase, the 45–47 kDa impurity as *C. difficile* glutamate dehydrogenase, and the 60–70 kDa protein as a homologue of groEL or the bacterial hsp60 family of proteins (~70% homology).

Good separation of Toxin A and Toxin B proteins is achieved using native PAGE gels, as confirmed by western blotting with anti-Toxin A and anti-Toxin B antibodies. As with the reducing gels, a number of lower molecular weight anti-Toxin B reactive bands are observed.

Toxin A can also be separated from Toxin B by ion exchange HPLC using a DEAE-5PW column. The Toxin A/Toxin B ratio is approximately 2.2, as measured by ELISA, and approximately 1.9, as measured by ion-exchange chromatography.

Alum-Adsorbed Toxoid Vaccine

We prepare alum for toxoid adsorption from commercially available sterile Rehydragel LV®, which contains 20 mg/ml aluminum oxide (Reheis, Inc., Berkeley Heights, N.J.). This material is first diluted to 3 mg/ml aluminum oxide with 50 mM phosphate buffer at pH 7.4, 100 mM NaCl, 100 mg/ml formaldehyde. The diluted alum is filled aseptically into sterile, pyrogen-free 10 ml capacity glass vials with gray butyl rubber stoppers under class 100 conditions.

Identification of Candidates for Vaccination to Generate *C. difficile* Immune Globulin Donors As is discussed above, *C. difficile* immune globulin donors can be generated by percutaneous administration of *C. difficile* toxoid vaccine. Preferred candidates for vaccination are subjects that already have *C. difficile* toxoid neutralizing antibodies. These donors have been exposed to toxin and would require fewer booster doses to reach useful titers. We have tested 9 commercial lots of intravenous immune globulin, and have found them to contain very low levels of neutralizing antibodies to *C. difficile* Toxin A and Toxin B. The titers of antitoxin in these preparations is <1:50 to both toxins, the titer being higher to Toxin B than to Toxin A. We also conducted a survey of 100 professional plasma donors from a center in Nevada. The results indicate that 2% and 13% of these individuals had antitoxin A and antitoxin B neutralizing antibodies, respectively, but at very low titers. These data show that selection of plasma from unstimulated, seropositive plasma donors for the purpose of preparing a hyperimmune human antitoxin to treat *C. difficile* would not be effective, and that it is necessary to stimulate donors by immunization with toxoid vaccine to produce a therapeutic human immune globulin.

TABLE 4

Antitoxin Antibody Levels in Plasma Donors (n = 100)

| Antigen | Assay* | Positive (%) | Mean** |
|---|---|---|---|
| Toxin A | ELISA (>0.2 OD) | 15 | 0.33 ± 0.14 |
| | Neutralization | 2 | 1:7.5 |
| Toxin B | ELISA (>0.2 OD) | 40 | 0.53 ± 0.37 |
| | Neutralization | 11 | 1:35 |

Preclinical Evaluation of Active and Passive Immunization Methods

Active Immunization of Mice

Groups of 8 female Swiss Webster mice were immunized intraperitoneally (IP) with 2 doses of alum-adsorbed toxoid vaccine one week apart. Toxoid was adsorbed to alum to mimic the human formulation (ratio of 0.144 mg protein per mg of aluminum). Doses were administered over a range of tenfold dilutions of adsorbed vaccine. Animals were dosed with four different toxoid lots for comparison of immunogenicity: one research lot (Lot 27–33) and three vaccine lots (Lots 133, 135, and 144) manufactured according to the method for production of the clinical product. One week after the second immunization, sera were tested for total antibody by ELISA, and for antibodies to Toxin A and Toxin B by cytotoxicity neutralization. In the cytotoxicity neutralization assay, toxins (10× $MC_{50}$) are incubated with twofold antibody dilutions for 1 hour at 37° C., and then inoculated onto monolayer cultures of IMR90 cells. Neutralization titer is expressed as the highest dilution of antibody that protects 50% of the cells from rounding.

ELISA data show that anti-toxin immunity develops in a dose-dependent manner. Toxin A appears slightly more immunogenic than Toxin B when the magnitude of response at a particular dilution of toxoid is compared. The toxoid also elicited neutralizing antibody responses. The dose of toxoid required to elicit neutralizing antibodies that protect cells from rounding is higher for Toxin B than for Toxin A, also demonstrating the higher immunogenicity of Toxin A in mice.

To determine whether toxoid vaccine protects mice against the lethal effects of Toxins A and B, groups of mice were immunized intraperitoneally with two weekly doses of vaccine. They were then challenged with five $LD_{50}$ of Toxin A (100 ng, IP) or Toxin B (200 ng, IV). Animals were monitored for illness and death for 14 days. Unimmunized animals died within the first 24 hours after challenge.

Results showed that mice were protected from Toxin A at a dose of adsorbed toxoid that contained >50 ng of protein and mice were protected from Toxin B at a dose of >5 mg. As in the immunogenicity experiment described above, Toxin A was protective at a dose 10–100 fold lower than that required to protect animals from Toxin B challenge.

The effect of alum on the immunogenicity of the toxoid was tested in mice. Groups of ten animals were immunized intraperitoneally with 3 weekly doses of soluble toxoid or toxoid adsorbed to alum. Alum adsorptions were performed immediately prior to dosing by mixing 0.144 mg toxoid protein per mg aluminum. Animals received 10 μg toxoid alone or 10 μg toxoid adsorbed to alum. Anti-toxin immune responses were measured by ELISA and cytotoxicity neutralization in serum samples. Total antibody titers determined by ELISA were comparable for soluble toxoid and alum adsorbed toxoid. Neutralizing antibody titers against both toxins were higher in groups that received alum adsorbed toxoid.

Mice are very sensitive to parenterally administered purified Toxin A and Toxin B, and thus can be used to monitor toxoid inactivation. The $LD_{50}$ of purified Toxin A and Toxin B tested individually are approximately 50 ng. The partially purified toxin preparation, prior to inactivation, has an $LD_{50}$ of less than 20 ng total protein, which corresponds to approximately 4–8 ng of each toxin, suggesting that the toxins may act synergistically when administered together.

Following inactivation with formalin, no toxicity is observed in mice when animals receive the largest dose of inactivated toxoid that has been administered, containing 1.25 mg total protein, corresponding to about 500 mg of Toxin A toxoid and 250 μg of Toxin B toxoid. These data show a minimum reduction in lethality of over $6.25 \times 10^4$ fold. The actual extent of inactivation is at least 8 orders of magnitude, as determined by a more sensitive tissue culture assay. The mouse safety assay is also used to define the duration of inactivation. Toxoid (0.5 mg) is typically fully tolerated at Days 5–6. Inactivation is stopped after three times the length of inactivation required to show no lethality in mice after a 0.5 mg intraperitoneal challenge.

Since vaccination protects the mouse from the biologic effects of Toxin A and Toxin B, the mouse model has been adapted to serve as the principal potency assay for the manufactured toxoid vaccine. In this assay, mice are immunized and then bled to recover serum, which is tested for toxin neutralization activity in vitro in the IMR90 tissue culture system.

Figure 7:
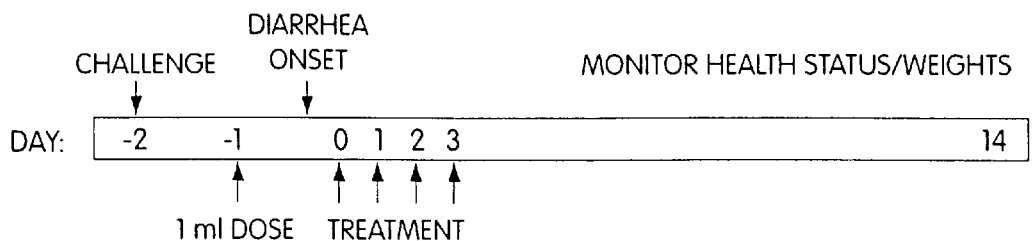
FIG. 7 is a schematic representation of a schedule for passive immunization of hamsters with diarrhea using *C. difficile* toxin-neutralizing antibodies.
Figure 8:
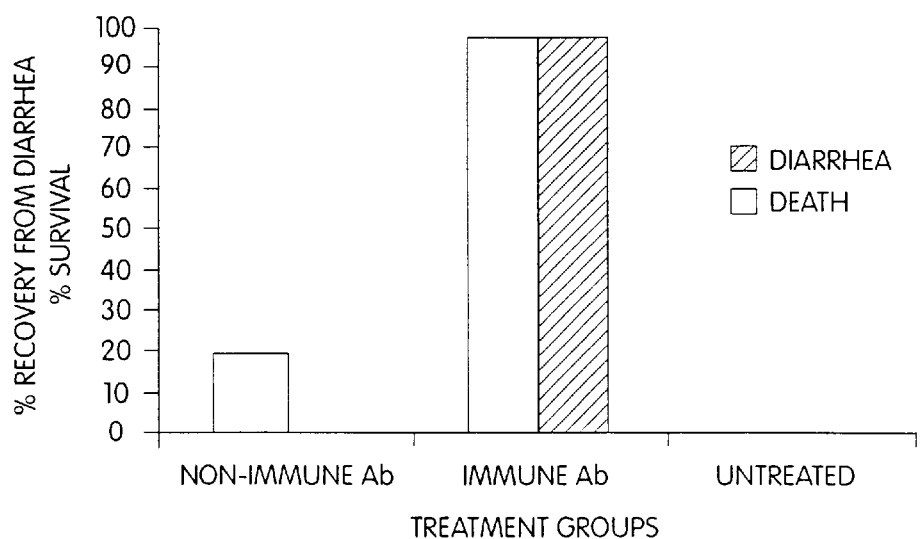
FIG. 8 is a graph showing that death and diarrhea are prevented in hamsters treated with *C. difficile* toxin-neutralizing antibodies.

To utilize this assay, we first determined that protection in mice correlates with in vitro neutralization activity, as measured in the IMR90 system. Four lots of toxoid vaccine were used to vaccinate mice intraperitoneally with two weekly doses. Toxoid was adsorbed to alum as described above and tested over a range of tenfold doses. Animals were bled 7 days after the second dose of vaccine and sera from individual mice was tested for its ability to neutralize the effects of Toxins A and B on IMR90 cells. Animals were allowed to recover for 4 days, and then challenged with lethal doses of either Toxin A or Toxin B. The correlation of neutralizing antibody titer and survival from challenge with both toxins was highly significant ($p<0.0001$ by the Wilcoxon Rank Sums Test).

Active Immunization of Hamsters

The hamster provides an excellent model of *C. difficile* infection, as this species is highly sensitive to the actions of Toxin A and Toxin B. After a single dose of clindamycin in the presence of *C. difficile*, hamsters die within 2–3 days with fulminant diarrhea and hemorrhagic cecitis. Hamsters immunized with the toxoid vaccine intramuscularly are protected from death and diarrhea when subsequently challenged with *C. difficile*. This route of immunization induces serum antibodies (IgG), but does not induce detectable mucosal antibodies, indicating that high titers of IgG can protect from the intestinal disease caused by *C. difficile.*

To quantitate the level of protection from death and diarrhea, groups of hamsters were vaccinated intramuscularly on days 0, 14, and 21 with approximately 100 μg of toxoid (A and B) in solution (n=15) or placebo (n=10). Two weeks after the final dose, hamsters were challenged intragastrically (IG) with 1.0 mg clindamycin followed by $1\times10^5$ *C. difficile* (ATCC strain 43255). Animals were monitored for weight loss, diarrhea, and survival for 14 days after challenge (FIG. 3). Hamsters immunized with toxoid vaccine were protected from death ($p\geqq0.0001$) and diarrhea ($p=0.0057$), compared to sham immunized controls (FIG. 4). When sera from each individual animal was analyzed, toxin-neutralizing antibody levels were present and correlated with protection.

Passive Immunization in Hamsters and Mice

Experiments in two animal models confirm the therapeutic efficacy of passive immunization. Treatment with toxin-neutralizing antibody preparations protects mice from lethal challenge. Utilizing the clindamycin challenge model described above, hamsters given toxin-neutralizing antibodies were shown to be protected from death and diarrhea. Hamsters developing diarrhea can be cured by parenteral administration of toxin-neutralizing antibodies. Protective therapeutic activity of passively administered antibody is dose-dependent and correlates with passive serum neutralizing antibody levels achieved in animals treated with the antibody containing preparation.

Passive Protection of Mice From Lethal Challenge

To test the protective capacity of toxin-neutralizing antibodies, mice were given hyperimmune mouse ascites containing antibodies to both Toxin A and Toxin B by the intraperitoneal (IP) route and then challenged with Toxin A or Toxin B. The mice received a single dose of pooled ascites at doses of 100, 10, or 1 μl, and were bled daily to determine the level of neutralizing antibodies passively obtained in serum. Animals were then challenged with Toxin A ($5\times LD_{50}$ IP) or Toxin B ($5\times LD_{50}$ IV) and monitored for 7 days. Direct administration of Toxin A and Toxin B leads to death in mice. The 100 μl dose of ascites protected 60% of animals against Toxin A and 80% of animals against Toxin B lethality. The mice were protected from Toxin A challenge for up to 23 days after antibody administration. Antibodies had to be administered within 30 minutes of toxin injection to obtain this level of protection from lethality. Laboratory measurements indicated all surviving animals had reciprocal serum neutralization titers of $\geqq200$ as a result of the infusion with ascites. The half-life of toxin-neutralizing antibodies was estimated to be 2 weeks, under the conditions of the study.

Passive Protection of Hamsters Following Clindamycin Challenge

Groups of female hamsters were given a single dose of hyperimmune mouse ascitic fluid IP. Graded doses were administered (6, 2, 0.6, or 0.2 ml ascites per animal). Ascites from non-immune mice served as a negative control. Animals were bled in order to measure passive serum antibody levels the day following receipt of the ascites and challenged with clindamycin 2 days later. Animals were monitored for 3 weeks after challenge for survival, diarrhea, and weight loss (FIG. 5). Protection against death was achieved in the three highest dose groups, and protection against both death and diarrhea was seen in animals receiving the highest dose of antibodies (FIG. 6). Levels of neutralizing antibodies correlated with protection from death and diarrhea. Fully protected animals had reciprocal serum neutralizing antibody of 800 with the least effective titer being 200. The half-life of neutralizing antibodies in hamster serum in this study was estimated to be 14 days.

Treatment of Diarrhea in Hamsters Using Neutralizing Antibodies

The hamster model of antibiotic-associated diarrhea is a useful one for the evaluation of prophylactic strategies against *C. difficile*. However, *C. difficile* disease is very severe in hamsters with acute cecitis and death occurring rapidly after clindamycin challenge. The severity of the infection can be reduced by the administration of a predetermined amount of neutralizing antibodies against Toxin A and Toxin B designed to protect from death but not diarrhea. The dose that prevents death but not diarrhea was defined in dose ranging experiments. During the period when animals had diarrhea, additional neutralizing antibodies could resolve the diarrhea. Animals given ascites from non-immune animals continued to suffer from diarrhea and most eventually died. Treated animals recovered from diarrhea within 24 hours after treatment, without relapse. The experimental design and diarrhea outcome are shown in FIGS. 7 and 8. This experiment shows that toxin-neutralizing antibodies can be used to treat *C. difficile* associated diarrhea. Recovery was rapid.

Immunogenicity of Toxoid Vaccine in Non-Human Primates

Figure 9:
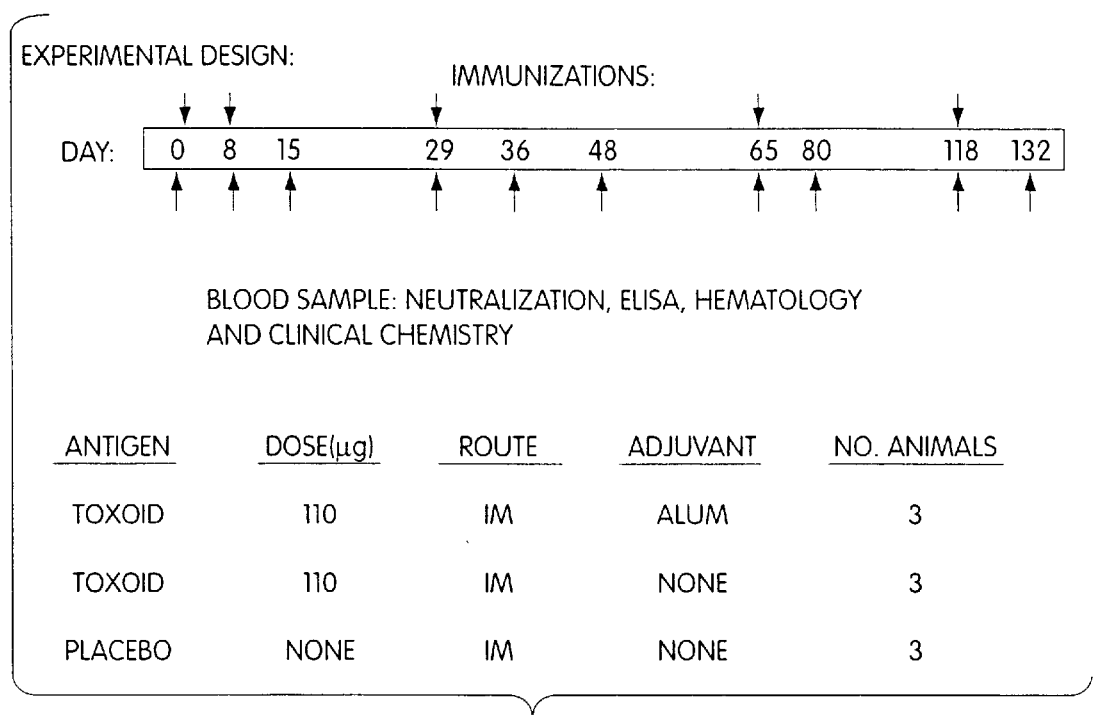
FIG. 9 is a schematic representation of experiments addressing the safety and immunogenicity of *C. difficile* toxoid vaccine in Rhesus monkeys.
Figure 10:
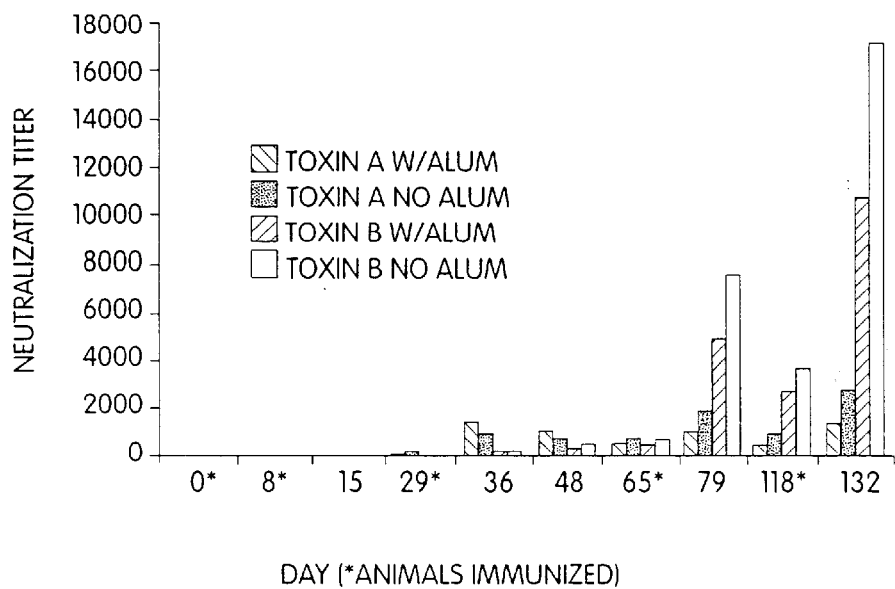
FIG. 10 is a graph showing the mean toxin-neutralizing antibody titers in Rhesus monkeys immunized with *C. difficile* toxoid vaccine.

Neutralizing antibodies to both Toxin A and Toxin B were induced in rhesus monkeys after immunization with our toxoid vaccine. Groups of 3 animals were given fluid vaccine, with either the vaccine adsorbed to alum or placebo. The study was designed to demonstrate the ability of the vaccine to raise high titer neutralizing antibodies in non-human primates. Placebo controls were included primarily for safety comparisons. Animals received 5 doses of vaccine (110 µg) in solution, adsorbed to alum, or placebo. Vaccine was administered on days 0, 8, 29, 65, and 118 in a 0.5 ml volume by the intramuscular route in the gluteal area. Immune response and clinical pathology were monitored (FIG. 9). No adverse pathology or sensitivities were noted after the 5 doses were given. All immunized animals responded with both binding and neutralizing antibodies. Several vaccine doses were required to induce significant neutralizing antibodies; a booster dose at days 65 and 118 raised neutralizing antibody levels further. Alum adsorbed vaccine induced more rapid and higher responses in some animals (FIG. 10). The studies showed the feasibility of inducing levels of neutralizing vaccine-induced antibodies suitable for processing into immune globulin preparation and documented the ability of booster doses in primed animals of eliciting high titers of protective antibodies. This experiment also demonstrated that hyper-immunization with multiple booster doses of toxoid was safe in non-human primates.

All referenced cited herein are incorporated by reference in their entirety. Other embodiments of the invention are within the following claims.

What is claimed is:

1. A method of producing human hyperimmune *Clostridium difficile* toxin-neutralizing immune globulin, said method comprising the steps of:

administering a *Clostridium difficile* toxoid to a human that already has *C. difficile* neutralizing antibodies; and isolating said *Clostridium difficile* toxin-neutralizing immune globulin from said human.

2. The method of claim 1, wherein said *Clostridium difficile* toxoid comprises a toxoid of toxin A and a toxoid of toxin B.

* * * * *